US009227200B2

(12) United States Patent
Chiou et al.

(10) Patent No.: US 9,227,200 B2
(45) Date of Patent: Jan. 5, 2016

(54) MICROFLUIDIC DEVICES WITH FLEXIBLE OPTICALLY TRANSPARENT ELECTRODES

(75) Inventors: Pei-Yu E. Chiou, Los Angeles, CA (US); Kuo-Wei Huang, Los Angeles, CA (US); Igor Y. Khandros, Orinda, CA (US); Ming C. Wu, Moraga, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 426 days.

(21) Appl. No.: 13/486,714

(22) Filed: Jun. 1, 2012

(65) Prior Publication Data

US 2012/0325665 A1    Dec. 27, 2012

Related U.S. Application Data

(60) Provisional application No. 61/493,334, filed on Jun. 3, 2011.

(51) Int. Cl.
*B03C 5/00* (2006.01)
*B03C 5/02* (2006.01)
*B82Y 30/00* (2011.01)

(52) U.S. Cl.
CPC .......... *B03C 5/026* (2013.01); *B03C 5/005* (2013.01); *B82Y 30/00* (2013.01); *B03C 2201/26* (2013.01)

(58) Field of Classification Search
CPC .................... B01L 3/5027–3/502715
See application file for complete search history.

(56) References Cited

PUBLICATIONS

D.-H. Lee, et al. "Generation and manipulation of droplets in an optoelectrofluidic device integrated with microfluidic channels", Applied Physics Letters, vol. 95, No. 16, Oct. 19, 2009, paper # 164102, p. 164102-1-164102-3.*
Huang, K.-W. et al. "Optoelectronic Tweezers Integration with Multilayer Microfluidic Device Using SWNT Embedded PDMS Membrane Electrode"—16th Int. Conf. Solid State Senors, Actuators and Microsystems, Jun. 5-9, 2011, pp. 1300-1303.
Zhou, Y. et al.—"A method for printing nanotube thin films"—Applied Physics letter, vol. 88, No. 12, Mar. 2006, pp. 123109-1-123109-3.
Hu, L. et al.—"Carbon Nanotube Thin Films: Fabrication, Properties, and Applications"—Chem. Rev., vol. 110, 2010, pp. 5790-5844.
Huang, K.-W. et al.—"Electrodes for Microfluidic Integrated Optoelectronic Tweezers"—Advances in OptoElectronics, vol. 2011, 2011, pp. 1-10.
Chiou, P.-Y. et al.—"Massively parallel manipulation of single cells and microparticles using optical images"—Nature, vol. 436, Jul. 21, 2005, pp. 370-372.
Ohta, A. et al.—"Dynamic Cell and Microparticle Control via Optoelectronic Tweezers"—Jour. of Microelectromechanical Systems, vol. 16, No. 3, Jun. 2007, pp. 491-499.

* cited by examiner

*Primary Examiner* — J. Christopher Ball
(74) *Attorney, Agent, or Firm* — John P. O'Banion (57) ABSTRACT

Microfluidic devices in which electrokinetic mechanisms move droplets of a liquid or particles in a liquid are described. The devices include at least one electrode that is optically transparent and/or flexible.

34 Claims, 8 Drawing Sheets

MICROFLUIDIC DEVICES WITH FLEXIBLE OPTICALLY TRANSPARENT ELECTRODES

CROSS-REFERENCE TO RELATED APPLICATIONS

This application is a nonprovisional of, and claims priority to, U.S. patent application No. 61/493,334 filed on Jun. 3, 2011, incorporated herein by reference in its entirety.

STATEMENT REGARDING FEDERALLY SPONSORED RESEARCH OR DEVELOPMENT

This invention was made with Government support under Grant No. ECCS-0747950 awarded by the National Science Foundation. The Government has certain rights in the invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to microfluidic circuit devices such as optoelectronic tweezers (OET) devices, and more particularly to electrode configuration in such devices.

2. Discussion

Optoelectronic tweezers (OET), dielectrophoresis (DEP), electrowetting, opto-electrowetting (OEW), electroosmosis, and electrophoresis devices are examples of technologies that utilize an electrokinetic mechanism to move particles, such as polystyrene beads, semiconductor microdisks, nanowires, DNA, cells, and liquids or liquid droplets. OET, for example, is a powerful technology that allows for massive parallel manipulation of single cells with light images at low light intensity. Cells are manipulated on an OET platform through light induced dielectrophoresis (DEP), a force exerted on a particle subjected to a non-uniform electric field. OET technology has been used for manipulating many types of particles, including polystyrene beads, semiconductor microdisks, nanowires, DNA, and cells. OEW technology has been used for manipulating liquid droplets on a platform through DEP forces. However, conventional OET and OEW platforms require a sandwich structures consisting of a photoconductive electrode and an ITO electrode for applying voltage. The ITO electrode prohibits OET from being integrated with many microfluidic components for conducting more complex multi-step protocols. On the other hand, Au-mesh electrodes have successfully enabled OET and OEW integration with multilayer PDMS microfluidic devices with valve functions. However, Au-mesh electrodes can withstand only a small amount of deformation and could fail after large deformation that induces cracks on the electrode. To realize OET and OEW integrated microfluidic devices as well as other types of devices that utilize electrokinetic mechanisms (e.g., DEP, electrowetting, opto-electrowetting, electrophoresis, or electroosmosis devices) capable of processing complex functions or to allow microscopic inspection or fluorescence detection, the electrode needs to be transparent, conductive, flexible, and/or capable of bonding strongly to OET, OEW, electrowetting, or DEP chips.

BRIEF SUMMARY OF THE INVENTION

Accordingly, we have developed a new fabrication method that allows embedding of single-walled carbon nanotube thin-film (SWNT) into PDMS, and formation of multiplayer PDMS microfluidic structures with optically transparent, electrically conductive, and mechanically deformable membrane valves. The valve permits repeated deformation without losing its conductivity. Furthermore, the SWNT embedded PDMS membrane can be deposited deep into the channel without residual carbon nanotubes remaining on the side wall that will affect local electric field distribution or on the bonding surface. This allows for a clean surface to form strong covalent bonding between OET and PDMS through regular oxygen plasma surface treatment. Our embedded single-walled carbon nanotube thin-film (SWNT) electrodes can be used as a conductive, transparent and flexible layers in poly (dimethylsilane) (PDMS), and our integration with optoelectronic tweezers allows for optical manipulation of microparticles or cells.

In some embodiments, an electrokinetic microfluidic device can include a first wall, a second wall, a chamber, and a biasing voltage source. The first wall can comprise a transparent electrode. The chamber can be configured to hold a liquid and can be between the first wall and the second wall. The biasing voltage source can be between the transparent electrode and the second wall and can create an electric field in the chamber between the transparent electrode and the second wall. The electric field can provide an electrokinetic mechanism for moving the liquid or a particle in the liquid in the chamber.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 5: (a) A microscopic image of SWNT embedded valves and channels in a multilayer PDMS microfluidic device. The channel is bonded on an OET chip; (b) SEM image of SWNT/PDMS composite surface; (c)(d) Bright field and fluorescence images of 10 μm fluorescence particles underneath a SWNT embedded electrode; (e)(f) Deformed SWNT membrane electrode closes the bottom channel. The flow channel height is 19 μm; (g) Measured sheet resistance of SWNT embedded PDMS electrode and its relation with optical transmittance at 632 nm.

FIG. 6: (a)(b) Transport of a 10-μm particle by light across a membrane valve on an OET integrated multilayer PDMS device. The scale bars are equal to 150 μm; (c) Comparison of particle moving speed in OET using ITO electrode and SWNT embedded PDMS electrode. The light intensity is 0.06 W/cm$^2$ and the applied frequency is 100 kHz.

DETAILED DESCRIPTION OF THE INVENTION

Device Configuration

Figure 1:
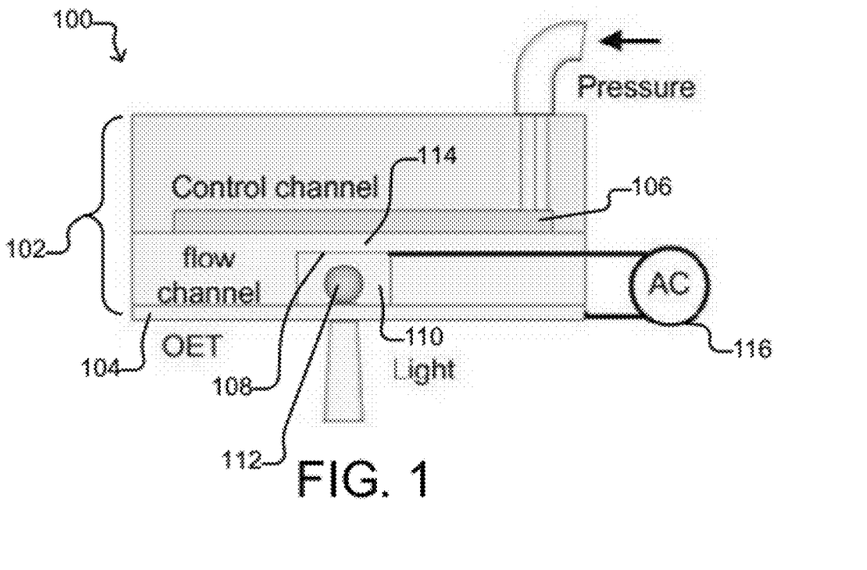
FIG. 1 is a schematic diagram of a generalized embodiment of a microfluidic integrated OET device according to the present invention.
Figure 2:
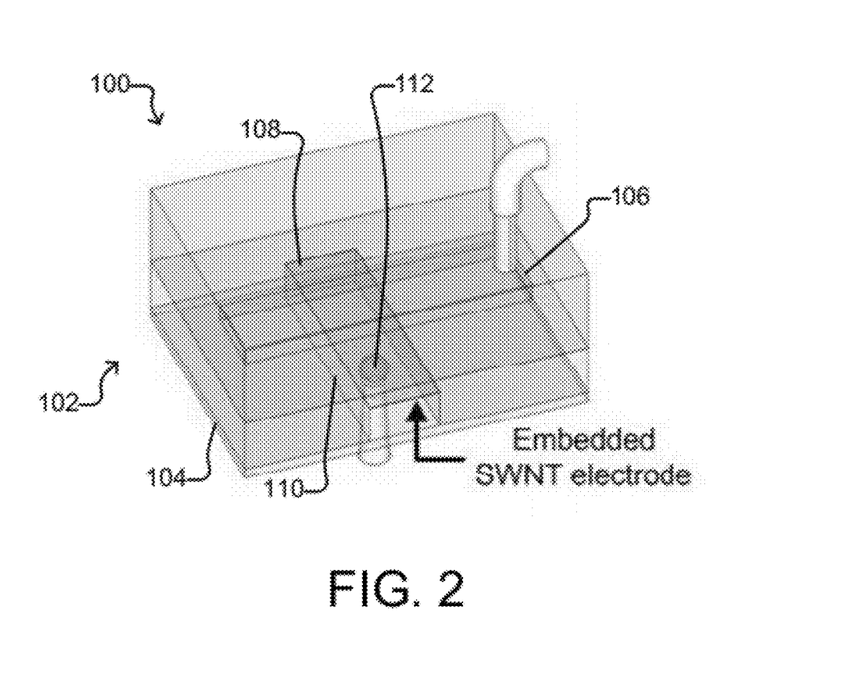
FIG. 2 is a schematic diagram of the device shown in FIG. 1 illustrating a SWNT embedded PDMS thin film electrode as the top channel surface and the deformable check valve according to an embodiment of the present invention.
Figure 3:
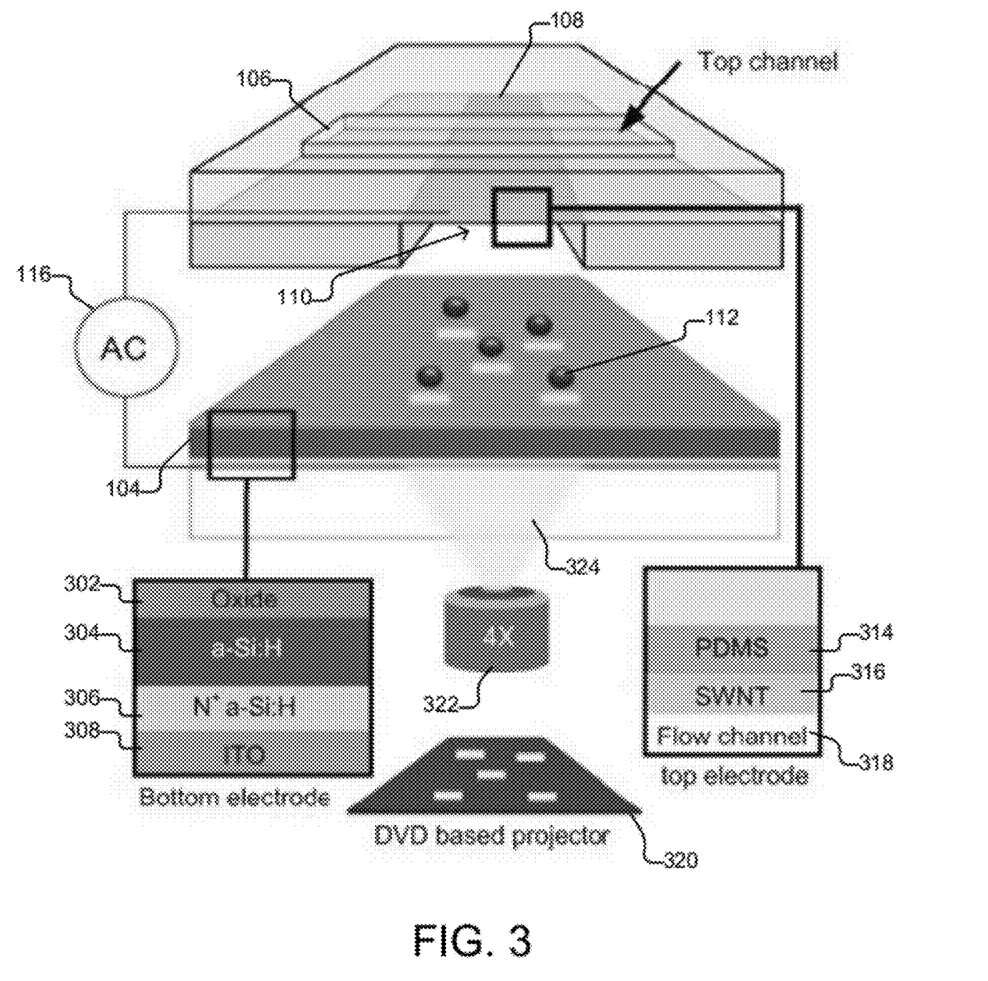
FIG. 3 is a detailed schematic diagram of a microfluidic integrated OET device using a SWNT embedded flexible PDMS electrode as the top channel surface and the deformable check valve according to an embodiment of the present invention.

FIG. 1 through FIG. 3 schematically illustrate the general configuration of an apparatus 100 that incorporates a microfluidic integrated optoelectronic tweezers (OET) device 102 (which is an example of an electrokinetic device) according to an embodiment of the present invention. In the embodiment shown in FIG. 1 through FIG. 3, the device 102 comprises an upper polydimethylsiloxane (PDMS) microfluidic channel 106, a bottom photoconductive OET substrate 104, an embedded transparent electrode 108 in the form of a single-walled nanotube (SWNT) thin-film electrode (which is an example of a mesh material), and a bottom channel 110. Unlike a conventional OET device in which a fluid chamber is formed between an indium tin oxide (ITO) electrode and a photoconductive substrate, our invention comprises a multilayer PDMS microfluidic integrated OET with two or more layers of channels 106, 110.

In one embodiment, the bottom channel 110 contains aqueous solutions carrying biological cells or particles 112 and the top channel 106 is used to control the membrane valve 114 (see FIG. 1) formed at the region where the upper channel 106 and bottom channel 110 intersect. In one embodiment, this elastic membrane 114 works as a mechanical valve that can be controlled by pneumatic pressure to close the bottom channel 110 and stop the fluid flow. In one embodiment, a peristaltic pump can be achieved by actuating three valves along a channel in series.

Referring more particularly to FIG. 3, in a preferred embodiment a multilayer bottom electrode is provided to establish the photoconductive OET substrate 104 (which is an example of a multilayer photoconductive wall). In the embodiment illustrated, these layers comprise an ITO layer 308, a 50-nm heavily doped n+ hydrogenated amorphous silicon (a-Si:H) layer 306 over the ITO layer, a photoconductive 1-μm undoped hydrogenated amorphous silicon a-Si:H layer 304 over the n+ a-Si:H layer, and a 100-nm silicon dioxide layer 302 over the undoped a-Si:H layer. The layer of silicon dioxide 302 is deposited for bonding with PDMS.

In the embodiment illustrated in FIG. 3, an embedded single-walled nanotube (SWNT) thin-film electrode 108 is fabricated on the top surface of the bottom PDMS channel 110. In this embodiment, electrode 108 comprises a composite SWNT 316/PDMS 314 thin film that establishes the top surface of the upper channel 110. Because SWNT/PDMS composite thin film exists only on the top surface of the channel 110, the surface for bonding with the OET substrate 104 is clean. This allows forming strong covalent bond with the silicon dioxide 302 coated OET substrate 104. Flow channel 318 is formed at the intersection of the upper 106 and bottom 110 channels.

For OET operation, an ac bias 114 is applied to the top SWNT electrode 108 and the bottom photoconductive electrode of the OET substrate 104. In the embodiment illustrated in FIG. 3, a Digital Micromirror Device (DMD) based projector 320 with an optional magnifying lens 322 is used to create dynamic optical images 324 and project it on the surface of the OET substrate 104 to generate virtual electrodes and induce DEP forces for cell and particle manipulation.

Device Fabrication

FIG. 4 illustrates a fabrication method that allows embedding SWNT thin film into PDMS and forming multiplayer PDMS microfluidic structures with optically transparent, electrically conductive, and mechanically deformable membrane valves according to an embodiment of the invention. The valve permits repeated deformation without losing its conductivity. Furthermore, SWNT embedded PDMS membrane can be deposited deep into the channel without residual carbon nanotubes remain on the side wall that will affect local electric field distribution or on the bonding surface, which gives a clean surface to form strong covalent bonding between OET and PDMS through regular oxygen plasma surface treatment.

Example 1

Figure 4A:
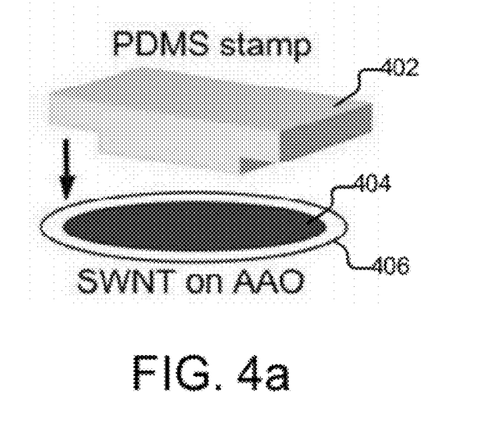
FIG. 4 is a schematic flow diagram of a fabrication process for embedding a thin layer of SWNT network in a multilayer PDMS microfluidic structure according to an embodiment of the present invention.
Figure 4B:
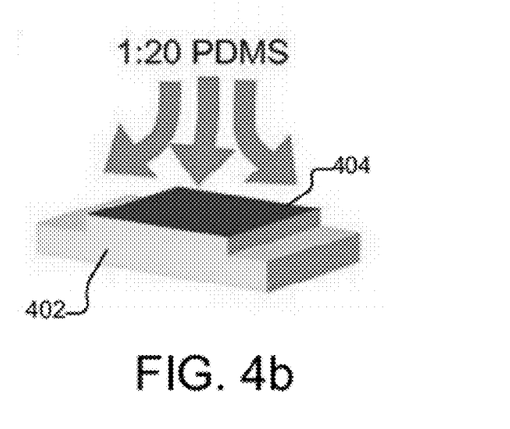
Figure 4C:
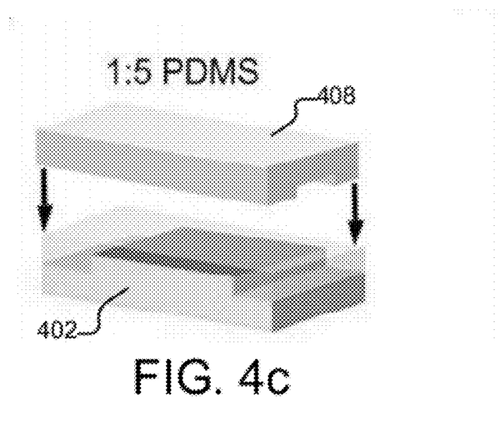
Figure 4D:
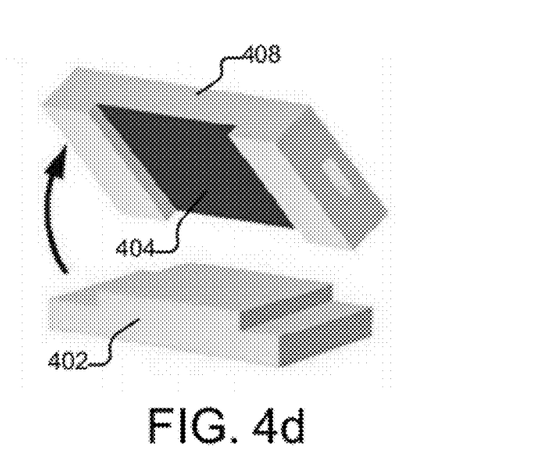

This fabrication method utilizes transfer-printing techniques and soft lithography to fabricate a transparent and flexible SWNT electrode on the top surface of PDMS channels. The process starts from disperse SWNT in DI water to form aqueous-based SWNT. Powders of commercial SWNT (Carbon Solutions, Inc.) are dissolved in 1 wt % sodium dodecyl sulfate (SDS) solution to prepare solution-based SWNT for vacuum filtration. After SWNT solution is sonicated and centrifuged, a porous anodic aluminum oxide (AAO) filter (Anodisc 47, Whatman Inc.) is used to obtain a SWNT network 404. For the PDMS stamp 402, a master mold was made by using standard photolithography processes with negative photoresist (SU-8 2025, MicroChem corporation) on a silicon wafer. Then Poly-dimethylsiloxance (Sylgard 184, Dow Corning) at the ratio 10 base:1 curing agent is poured onto the master mold and cured. The PDMS stamp 402 with patterns of microfluidic channels are treated by trichloro(1H, 1H, 2H, 2H-perfluorooctyl)silane (Sigam-Aldrich, Inc.). The treated PDMS stamp 402 is pressed to contact the AAO filter 406 (FIG. 4a). After the PDMS stamp 402 is removed from the filter 406, the SWNT thin film 404 is transferred onto the PDMS surface. The PDMS stamp 402 with the SWNT thin film 404 was used as the mold for the next casting step. Uncured PDMS with a ratio of 20 base:1 curing agent spin coated on the PDMS mold to create a thin PDMS film (FIG. 4b). Another thick PDMS layer made at the ratio of 5 base:1 curing agent is poured on the thin layer. The two layers are bonded after curing (FIG. 4c). The cured PDMS 408 can be peeled off from the mold 402 and the SWNT thin film 404 is transferred and embedded into the PDMS channels of the cured PDMS 408 (FIG. 4d).

Example 2

A vacuum filtration method is used to get uniform SWNT thin films. The suspension of SWNT is filtered through a filtration membrane to form a thin layer of SWNT network. The highly dense SWNT suspension was made by high purity (>90%) arc discharge nanotubes from Carbon Solutions, Inc. SWNT were dissolved in 1 wt % sodium dodecyl sulfate (SDS) solution to prepare solution-based SWNT. This highly concentrated SWNT suspension was ultrasonically agitated using a probe sonicator for ~10 minutes. To remove the carbon particles and impurities, the suspension was centrifuged at 14000 rpm for 30 min. A porous anodic aluminum oxide (AAO) filter (Anodisc 47, Whatman Inc.) was used in vacuum filtration. The suspension flows through the pores and leaves a thin film of a SWNT network on the surface of the AAO filter. The concentration and the volume of the flow suspension can control the density of SWNT network.

A PDMS stamp 402 was then used to transfer the SWNT thin film 404 from the filter 406. To fabricate the PDMS stamp 402, a master mold was made by using standard photolithography using a negative photoresist (SU-8 2025, MicroChem corporation) on a silicon wafer. Poly-dimethylsiloxane (Sylgard 184, Dow Corning) with a ratio of 10 base:1 curing agent was poured onto the master mold and cured at 65° C. for 4 hr. A PDMS stamp 492 with a pattern of microfluidic channels could be peeled off from the Si wafer. Before the stamp contact the filtration membrane, it was treated by trichloro (1H, 1H, 2H, 2H-perfluorooctyl)silane (Sigam-Aldrich, Inc.), a chemical release agent that lowers the adhesive forces between the PDMS stamp 402 and the SWNT thin film 404. The treated PDMS stamp 402 was then pressed in contact with the SWNT network 404 on the AAO filter 406 (FIG. 4a). After the PDMS stamp 402 is removed, the SWNT thin film 404 is transferred onto the extruding surface of the PDMS stamp 402. This PDMS stamp 402 with a SWNT thin film 404 was then used as the mold for casting microfluidic channels.

To cast the microfluidic channels, an uncured PDMS precursor at the ratio of 10 base:1 curing agent was poured onto the PDMS stamp 402, and baked in an oven. The uncured gel-like PDMS precursor infiltrates the vacant regions in the SWNT thin film 404 during the curing process. The cured microfluidic channels 408 were then be peeled off from the PDMS stamp 402 with a SWNT thin film 404 embedded near the top surface of channels. This fabrication technique can be used to embed SWNT thin film on multilayer PDMS microfluidic devices. To achieve that, the uncured PDMS precursor at a ratio of 20 base:1 curing agent was spin-coated on the PDMS stamp 402 to create a thin membrane (FIG. 4b). A top thick PDMS layer made with a ratio of 5 base:1 curing agent is pressed to contact the thin PDMS layer. These two layers are bonded after cured (FIG. 4c). The cured PDMS 408 with a top control channel and a thin film SWNT 404 embedded bottom PDMS channel can be peeled off from the first PDMS stamp 402 as shown in FIG. 4d. This multilayer PDMS channels 408 with an embedded SWNT thin film electrode 404 on the top surface of bottom channels including the membrane valve locations was then bonded with an OET device through oxygen plasma treatment.

Note that, in the examples above, the PDMS stamp 402 is not only used as the mold for casting other microfluidic channels but also transferring a SWNT thin film 404 to the top surface of a channel. This fabrication process is compatible with the standard soft lithography process. Since the SWNT electrode exists only on the top surface of the flow channels, this provides for a clean surface for forming strong covalent bonding between PDMS and silicon dioxide surface of an OET device. The electrode is continuous, optically transparent, electrically conductive and has robust mechanical flexibility allowing large deformation without failure.

Demonstration of SWNT Electrodes Embedded in PDMS

Figure 5A:
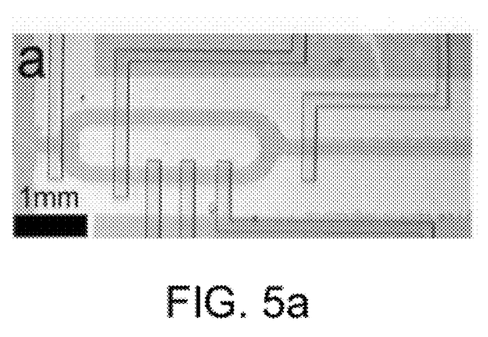
Figure 5B:
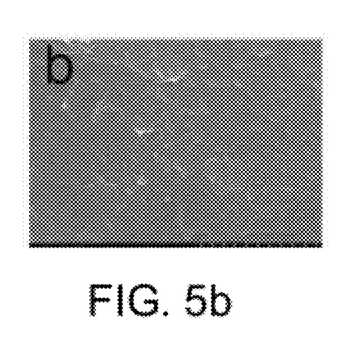

FIG. 5a shows the microscopic image of the SWNT electrode embedded in a multiplayer PDMS microfluidic device. This device has two layers of microfluidic channels. The ring-shape pattern is the bottom channel with SWNT electrodes embedded for sample delivery and cell manipulation. The top channel is used to deliver pressure to deform the membrane valves for closing a microfluidic chamber or pumping fluid in the bottom channel. FIG. 5b is the SEM image of a SWNT/PDMS composite electrode showing that the randomly distributed SWNT network is completely fixed in the cured PDMS matrix.

Figure 5C:
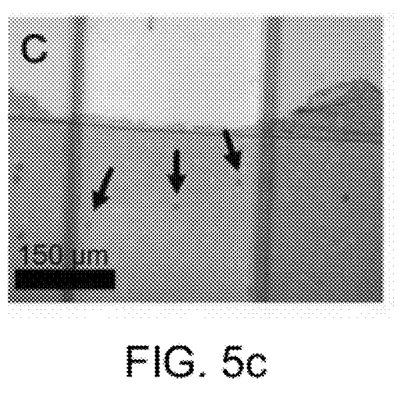
Figure 5D:
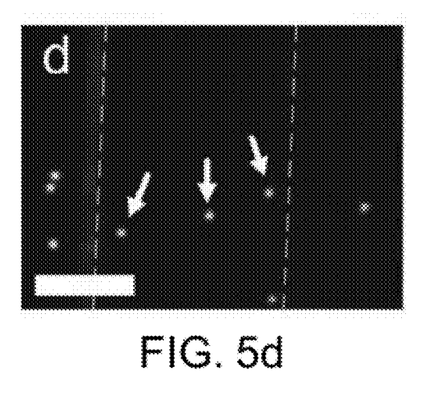

Because the a-Si layer on the microfluidic integrated OET is non-transparent to short wavelength visible light, fluorescence analysis has to come from the top SWNT/PDMS electrode, which one of the reason that this electrode needs to be transparent. FIG. 5c and FIG. 5d are the bright field and the fluorescence images of 10-μm fluorescent particles underneath the SWNT electrode. Three particles marked by arrows are located at the intersection of the top and the bottom channels separated by a ~50 μm thick SWNT/PDMS membrane. Comparison between the bright field and the fluorescence images shows fluorescent analysis is achievable via SWNT electrodes.

The transmission measurement is conducted by using a HeNe laser (wavelength=633 nm, power=2 mW, THORLAB). The relation between the measured sheet resistance and transmittance of embedded SWNT thin films are plotted in FIG. 5g. The transparency and the sheet resistance can be controlled by the thickness of the SWNT network, while the thickness can be adjusted by tuning the amount of SWNT dispersed in solution.

Figure 5E:
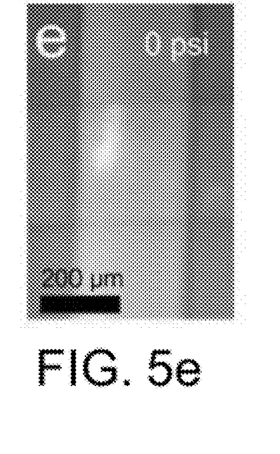
Figure 5F:
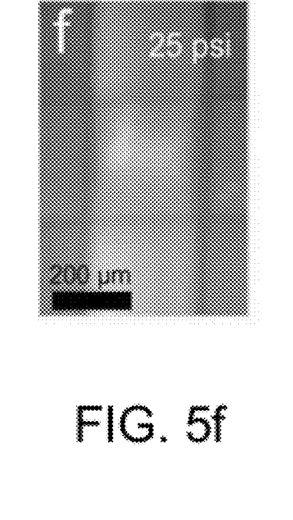
Figure 5G:
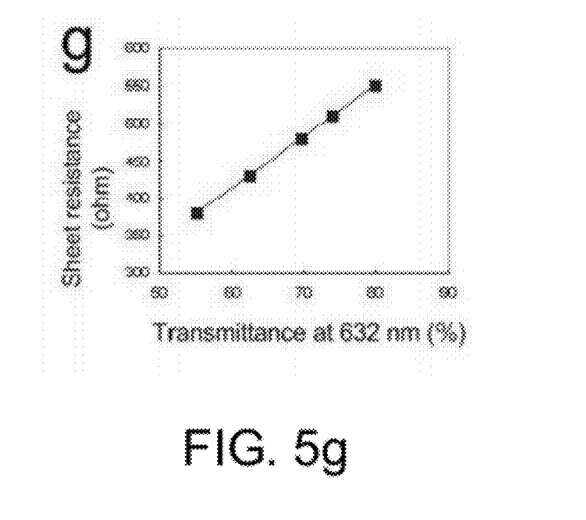

To evaluate the resistance change of the SWNT electrode after deformation, the SWNT/PDMS membrane valve was deformed by pressurizing the control channel repeatedly (FIG. 5e and FIG. 5f). The valve can be pushed down and closed by applying a pressure of 25 psi in the top control channels while the pressure in the bottom flow channel is 2 psi. The area of the valve is 300 μm×300 μm and the thickness of membrane is ~50 μm. The channel height of the bottom channel is 19 μm. The SWNT/PDMS membrane electrodes are still conductive after deforming for 30 times. This demonstrates that the SWNT/PDMS electrode is ideal for integrating OET with multilayer PDMS based microfluidic devices to not only supply electrical signals but also provide valve and pump functions that are required for conducting multi-step and complex protocols.

OET Manipulation

Figure 6A:
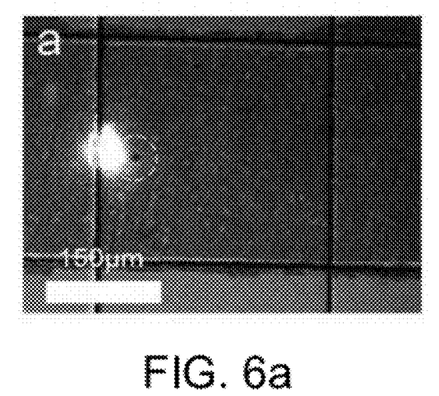
Figure 6B:
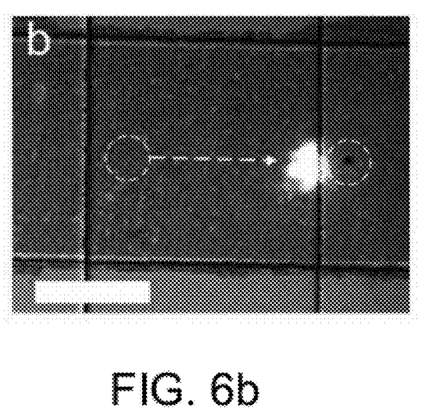

To verify the microfluidic integrated OET platform, we coupled a DMD based projector (BenQ, MP730) with an inverted microscope. The projection lenses of the projector are removed and replaced by a 4× objective lens to focus the light images on the photoconductive surface. 10-μm particles were firstly suspended in PBS buffer (conductivity=186 μS/cm) and flowed into the microchannels using syringe pumps. The microfluidic integrated OET was connected to a function generator (AGILENT 33220A) for supplying sinusoidal ac bias (100 kHz, 10 Vpp). Virtual electrodes were turned on by a projected light. Particles experienced negative DEP forces and repelled away from the light spots. FIG. 6a and FIG. 6b are the consecutive images showing a 10-µm particle is transported across a deformable PDMS membrane valve by the projection light.

Figure 6C:
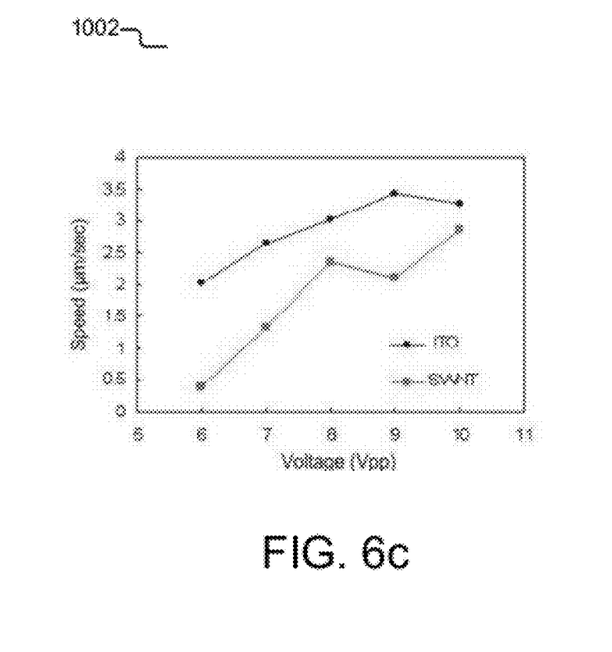

The performance of using a SWNT PDMS electrode for OET manipulation has been compared with a regular ITO electrode. The tests were under the application of various voltages at 100 kHz. The results are shown in FIG. 6c. This experiment is conducted on an inverted microscope and the light beam for OET manipulation pass through the SWNT/PDMS electrode before illuminating on the photoconductive surface. The SWNT/PDMS electrode absorbs part of the light, and only 60% of light is transmitted. This contributes to the slightly lower particle speed of OET manipulation using the SWNT/PDMS electrode.

CONCLUSION

We have successfully demonstrated a novel manufacturing method to fabricate an enabling SWNT/PDMS electrode that is transparent, flexible, deformable, and able to integrate OET with multilayer PDMS microfluidic device. The method can transfer SWNT thin film onto the top surfaces of PDMS channels without leaving any residuals on the sidewall that could affect the local electric field distribution and on the bonding surface, which leaves a clean PDMS interface to forming strong covalent bonding with the silicon dioxide coated OET surface for tight sealing. SWNT/PDMS electrodes with sheet resistance between 350~550 ohm and optical transmittance of 55% to 80% have been successfully fabricated. OET manipulation on an integrated PDMS based multilayer microfluidic device has also been tested and compared with conventional ITO electrodes. A valve closing function using SWNT/PDMS membrane has also been shown, and no degradation of electrical conductivity was observed of after repeated deformation for 30 times. The results show that SWNT electrodes solve the cracking problems of prior Au mesh electrodes. The microfluidic integrated OET has potential applications for high throughput, multistep cell-based analysis in the future.

Although the description above contains many details, these should not be construed as limiting the scope of the invention but as merely providing illustrations of some of the presently preferred embodiments of this invention. For example, although flexible, optically transparent electrodes 108 are illustrated and discussed in the examples above as comprising SWNT material and being used in an OET device, the flexible, optically transparent electrodes 108 of the present invention can comprise other materials and can be used in other types of devices.

For example, the flexible, optically transparent electrode 108 of the present invention can alternatively comprise materials such as multi-walled nanotubes. As another example, the electrode 108 can comprise other types of nanomaterials such as electrically conductive (e.g., metal) nanowires or clusters or electrically conductive (e.g., metal) nanoparticles or a combination of the foregoing (e.g., a combination of nanowires and nanoparticles). As yet another example, the electrode 108 can comprise a flexible, optically transparent material such as a polymer or a silicone with embedded nanomaterials such as electrically conductive (e.g., metal) nanowires or clusters or electrically conductive (e.g., metal) nanoparticles or a combination of the foregoing (e.g., a combination of nanowires and nanoparticles). Thus, the electrode 108 discussed above as comprising an SWNT material can alternatively be an electrode that comprises any of the forgoing materials (all of which are examples of a mesh material).

Figure 8:
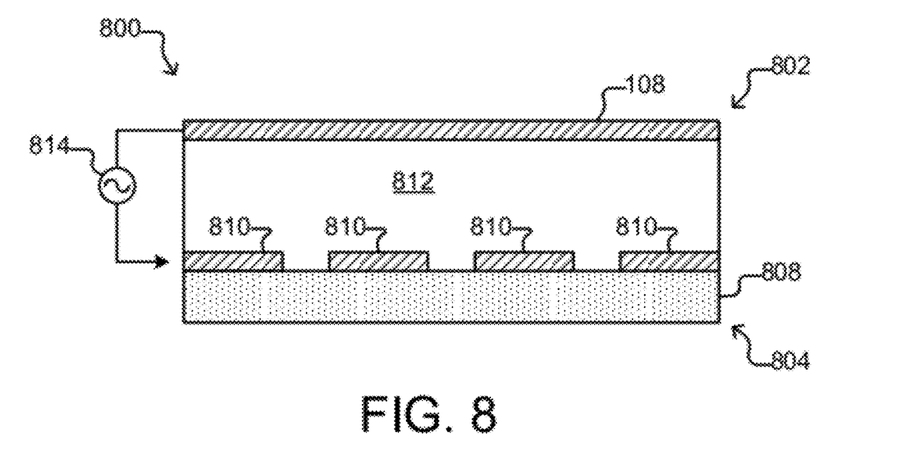
FIG. 8 and FIG. 9 illustrate additional examples of electrokinetic devices.
Figure 9:
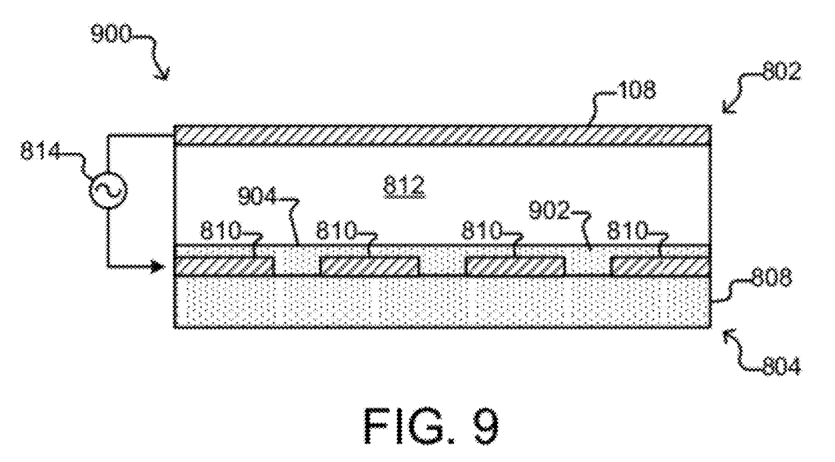

Examples of other types of devices that can include the flexible, optically transparent electrode 108 of the present invention include devices that use an electrokinetic mechanism to move a liquid (e.g., a droplet of the liquid) and/or a particle (e.g., objects, cells, or the like) in a liquid disposed between electrically biased walls. In such devices, an electrode in one or both of two such electrically biased walls can be a flexible FIG. 7 through FIG. 9 illustrate examples of such devices.

Figure 7:
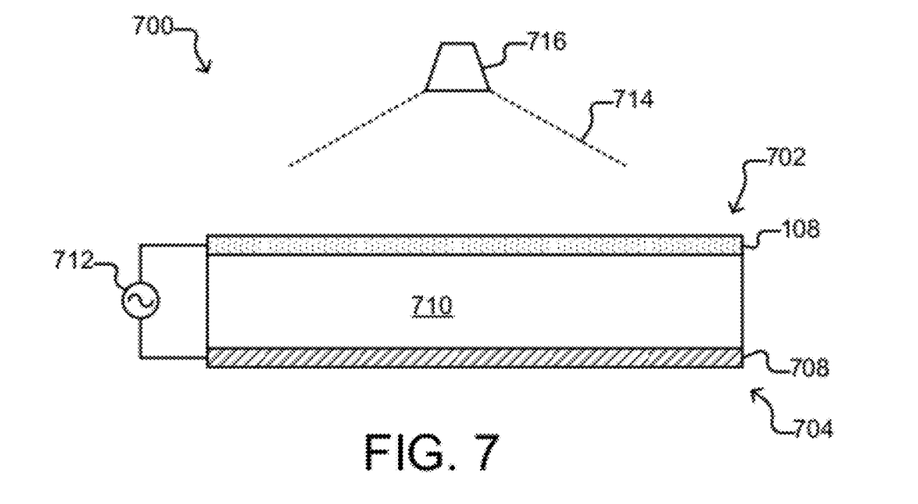
FIG. 7 illustrates a light controlled electrokinetic device of which the OET device of FIG. 1 through FIG. 3 is an example.

FIG. 7 illustrates a light-induced microfluidic electrokinetic device 700 that can comprise a chamber 710 disposed between a first wall 702 comprising a transparent electrode 108 and a second wall 704 comprising a photoconductive layer 708. The chamber 710 can be sufficiently enclosed to hold a liquid. As shown, a biasing voltage source 712 (e.g., an alternating current or a direct current voltage source) can be applied to the electrode 108 and the second wall 704 (e.g., the photoconductive layer 708). The voltage source 712 can create an electric field in the chamber 710 between the first wall 702 and the second wall 704.

In some embodiments, the device 700 can be an OET device. Generally in accordance with the discussion of OET above, light directed onto the photoconductive layer 708 can selectively create virtual electrodes at the photoconductive layer 708 that induce DEP forces that move particles in a liquid in the chamber 710. This is an example of an electrokinetic mechanism for moving particles in the liquid in the chamber 710. A light source 716 can provide patterns of light 714 through the transparent electrode 108 to the photoconductive layer 708 to selectively create such virtual electrodes.

In other embodiments, the device 700 can be an OEW device. The second wall 704 can comprise, in addition to the photoconductive layer 708, an optoelectronic wetting surface (not shown), which can have a hydrophobic coating (not shown), that faces into the chamber 710. The light pattern 714 projected onto the photoconductive layer 708 can selectively create virtual electrodes at the photoconductive layer 708 that induce electrowetting forces that move a liquid (e.g., a droplet of the liquid) on the optoelectronic wetting surface (not shown) in the chamber 710. This is an example of an electrokinetic mechanism for moving the liquid (e.g., a droplet of the liquid) in the chamber 710.

FIG. 8 illustrates a microfluidic DEP device 800 (which is an example of an electrokinetic device) that can comprise a chamber 812 between a first wall 802 comprising a transparent electrode 108 and a second wall 804 comprising a substrate 808 and an array of fixed electrodes 810. The chamber 812 can be sufficiently enclosed to hold a liquid. A biasing voltage source 814 can be applied to the transparent electrode 108 and selectively applied to one or more of the electrodes 810 in the electrode array on the substrate 808. By selectively connecting and disconnecting the biasing voltage source 814 to and from different ones of the electrodes 810, electric fields, which induce DEP forces, can be created in the chamber between selected ones of the electrodes 810 and the transparent electrode 108. The DEP forces can move particles in a liquid in the chamber 812. For example, by selectively connecting and then disconnected a sequence of the electrodes 810 to the biasing voltage source 814, a particle in a liquid in the chamber 812 can be moved from one electrode 810 to another electrode 810 and thus moved in the chamber 812. This is an example of an electrokinetic mechanism for moving particles in the liquid in the chamber 812.

Because the electrode 108 is transparent, movement of particles in the chamber 808 can be observed. For example, optical monitoring equipment (e.g., a camera) (not shown) can capture through the transparent electrode 108 images of particles in the chamber 812.

FIG. 9 illustrates a microfluidic electrowetting device 900 (which is an example of an electrokinetic device) that can be similar to device 800 except that device 900 can include an insulating material 902 disposed on the substrate 804 and over the fixed electrodes 810. The material 902 can have a surface 904, which can have a hydrophobic coating (not shown). As shown, the insulating material 902 can cover the electrodes 810. The electrowetting device 900 can operate generally like the device 800 except the electrowetting device 900 can move a liquid (e.g., droplets of the liquid) in the chamber 812. For example, by selectively connecting and disconnecting the biasing voltage source 814 to different ones of the fixed electrodes 810, electric fields, which induce electrowetting forces, can be selectively created in the chamber 812 between selected ones of the fixed electrodes 806 and the transparent electrode 108. The electrowetting forces can move the liquid (e.g., droplets of the liquid) on the surface 904 in the chamber 812 from one fixed electrode 810 to another electrode 810. This is an example of an electrokinetic mechanism for moving the liquid (e.g., droplets of the liquid) in the chamber 812, and the surface 904 is an example of an optoelectronic wetting surface.

It is noted that that the devices illustrated in FIG. 1 through FIG. 3 and FIG. 7 through FIG. 9 are examples only and can, for example, include additional and/or different elements, and the elements shown can be arranged in different configurations. Also, those devices can be in different orientations. For example the devices shown in FIG. 1 through FIG. 3 and FIG. 7 through FIG. 9 can be rotated (e.g., can be upside down) in alternative configurations.

From the discussion above it will be appreciated that the invention can be embodied in various ways, including but not limited to the following:

1. A microfluidic integrated OET apparatus, comprising: an upper PDMS chamber with an embedded SWNT thin film electrode; and a lower photoconductive OET surface, the photoconductive OET providing a lower electrode.

2. The apparatus of embodiment 1, wherein the lower electrode comprises: an ITO layer; a 50-nm heavily doped n+ hydrogenated amorphous silicon (n+ a-Si:H) layer over the ITO layer; a photoconductive 1-μm undoped hydrogenated amorphous silicon (a-Si:H) layer over the n+ a-Si:H layer; and a 100-nm silicon dioxide layer over the undoped a-Si:H layer.

3. The apparatus of embodiment 2, wherein the silicon dioxide layer facilitates bonding with PDMS.

4. The apparatus of embodiment 1: wherein the PDMS chamber has a bottom PDMS channel; wherein the bottom channel has a top surface; and wherein the SWNT embedded PDMS thin film electrode is fabricated on the top surface of the bottom PDMS channel.

5. The apparatus of embodiment 2: wherein for operating this device, an ac bias is applied to the embedded SWNT thin film electrode and the lower OET photoconductive electrode; wherein when light beams illuminate the a-Si:H layer, virtual electrodes are turned on to create non-uniform electric field between the lower light-patterned virtual electrode and embedded SWNT thin film electrode for DEP manipulation; and wherein when a virtual electrode is turned on by a projected light beam, cells or particles experiencing DEP forces are moved away or attracted to the light pattern.

6. A method for fabricating a PDMS microfluidic channel with an embedded SWNT thin film electrode, comprising: preparing a SWNT solution; collecting an SWNT network from said solution with an AAO filter; preparing a PDMS stamp as a mold for a microfluidic chamber, said PDMS stamp having an upper mold surface; contacting the AAO filter with the upper mold surface of the stamp, wherein the SWNT network is transferred onto the upper mold surface; spin coating a thin layer of PDMS over the SWNT network; forming a thicker layer of PDMS over the thin layer, wherein the thin and thicker layers bond after curing and form a molded structure with a PDMS microfluidic channel; and removing the molded structure from the mold; wherein the SWNT network is transferred and embedded into the PDMS microfluidic channel.

7. An electrokinetic microfluidic device, comprising: a first wall comprising a transparent electrode; a second wall; a chamber between said first wall and said second wall, said chamber configured to hold a liquid; and a biasing voltage source between said transparent electrode and said second wall for creating an electric field in said chamber between said transparent electrode and said second wall for providing an electrokinetic mechanism for moving said liquid or a particle in said liquid in said chamber.

8. The device of embodiment 7: wherein said chamber comprises a flexible mesh material disposed on said second wall; and wherein said transparent electrode is flexible and embedded in said flexible material.

9. The device of embodiment 8, wherein said chamber is sufficiently flexible to be pinched closed.

10. The device of embodiment 9: wherein said transparent electrode is sufficiently flexible to flex with said chamber as said chamber is pinched closed; and wherein said transparent electrode remains electrically conductive as said chamber is pinched closed.

11. The device of embodiment 8: wherein said second wall comprises a photoconductive layer disposed on a conductive layer; and wherein said biasing voltage is connected to said conductive layer.

12. The device of embodiment 8, wherein said flexible material comprises a PDMS material.

13. The device of embodiment 12, wherein said second wall further comprises an outer material that facilitates bonding with said PDMS material.

14. The device of embodiment 8, wherein said transparent electrode is a thin film, mesh electrode.

15. The device of embodiment 8, wherein said transparent electrode comprises nanoparticles.

16. The device of embodiment 15, wherein said nanoparticles comprise nanotubes or nanowires.

17. The device of embodiment 7, wherein said second wall comprises a photoconductive layer responsive to light passed through said transparent electrode to create virtual electrodes that induce DEP forces sufficient to move a particle in said liquid.

18. The device of embodiment 7, wherein said second wall comprises: a photoconductive layer; and an optoelectronic wetting surface that is an inner surface of said chamber.

19. The device of embodiment 18, wherein said photoconductive layer of said second wall is responsive to light passed through said transparent electrode to create virtual electrodes that induce DEP forces that move a droplet of said liquid in said chamber.

20. The device of embodiment 7, wherein said second wall comprises an array of fixed electrodes each selectively connectable to said biasing voltage source.

21. The device of embodiment 20, wherein said second wall further comprises an insulating material covering said fixed electrodes.

22. The device of embodiment 7, wherein said transparent electrode is a thin film, mesh electrode.

23. The device of embodiment 7, wherein said transparent electrode comprises nanoparticles.

24. The device of embodiment 23, wherein said nanoparticles comprise nanotubes or nanowires.

25. The device of embodiment 7, wherein said transparent electrode comprises clusters of nanoparticles.

26. The device of embodiment 7, wherein said transparent electrode comprises nanoparticles embedded in a flexible material.

27. The device of embodiment 26, wherein said flexible material is a polymer or a silicone.

28. The device of embodiment 7, wherein said transparent electrode comprises a combination of nanowires and nanoparticles embedded in a flexible material.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A microfluidic integrated optoelectronic tweezers (OET) apparatus, comprising:
    an upper polydimethylsiloxane (PDMS) chamber with an embedded single-walled nanotube (SWNT) thin film electrode; and
    a lower photoconductive OET surface, the photoconductive OET providing a lower electrode.

2. An apparatus according to claim 1, wherein the lower electrode comprises:
    an indium tin oxide (ITO) layer;
    a 50-nm heavily doped n-F hydrogenated amorphous silicon (n+a-Si:H) layer over the ITO layer;
    a photoconductive 1-μm undoped hydrogenated amorphous silicon (a-Si:H) layer over the n+a-Si:H layer; and
    a 100-nm silicon dioxide layer over the undoped a-Si:H layer.

3. An apparatus according to claim 2, wherein the silicon dioxide layer facilitates bonding with PDMS.

4. An apparatus according to claim 1:
    wherein the PDMS chamber comprises a PDMS channel;
    wherein the channel has a top surface; and
    wherein the SWNT embedded PDMS thin film electrode is fabricated on the top surface of the PDMS channel.

5. An apparatus according to claim 2:
    wherein for operating this device, an alternating current (AC) bias is applied to the embedded SWNT thin film electrode and the lower OET photoconductive electrode;
    wherein when light beams illuminate the a-Si:H layer, virtual electrodes are turned on to create non-uniform electric field between the lower light-patterned virtual electrode and embedded SWNT thin film electrode for dielectrophoresis (DEP) manipulation; and
    wherein when a virtual electrode is turned on by a projected light beam, cells or particles experiencing DEP forces are moved away or attracted to the light pattern.

6. The apparatus of claim 1, further comprising:
    an upper control PDMS channel, wherein at least a portion of the upper control PDMS channel is located above a region where at least a portion of the upper PDMS chamber is located.

7. A method for fabricating a polydimethylsiloxane (PDMS) microfluidic channel with an embedded single-walled nanotube (SWNT) thin film electrode, comprising:
    preparing a SWNT solution;
    collecting an SWNT network from the solution with an anodic aluminum oxide (AAO) filter;
    preparing a PDMS stamp as a mold for a microfluidic chamber, the PDMS stamp having an upper mold surface;
    contacting the AAO filter with the upper mold surface of the stamp, wherein the SWNT network is transferred onto the upper mold surface;
    spin coating a thin layer of PDMS over the SWNT network;
    forming a thicker layer of PDMS over the thin layer, wherein the thin and thicker layers bond after curing and form a molded structure with a PDMS microfluidic channel; and
    removing the molded structure from the mold;
    wherein the SWNT network is transferred and embedded into the PDMS microfluidic channel.

8. An electrokinetic microfluidic device, comprising:
    a first wall comprising a flexible mesh transparent electrode;
    a second wall; and
    a chamber between said first wall and said second wall, said chamber configured to hold a liquid;
    wherein an electric field can be created in said chamber by placing a biasing voltage source between said transparent electrode and said second wall, said electric field providing an electrokinetic mechanism for moving said liquid or a particle in said liquid in said chamber.

9. The device of claim 8:
    wherein said chamber is partially defined by a flexible material disposed on said second wall; and
    wherein said transparent electrode is flexible and embedded in said flexible material.

10. The device of claim 9, wherein said flexible material partially defining said chamber is sufficiently flexible to allow said chamber to be pinched closed.

11. The device of claim 10:
    wherein said transparent electrode is sufficiently flexible to flex with said flexible material as said chamber is pinched closed; and
    wherein said transparent electrode remains electrically conductive as said chamber is pinched closed.

12. The device of claim 9:
    wherein said second wall comprises a photoconductive layer disposed on a conductive layer; and wherein said biasing voltage source can be connected to said conductive layer.

13. The device of claim 9, wherein said flexible material comprises a polydimethylsiloxane (PDMS) material.

14. The device of claim 13, wherein said second wall further comprises an outer material that facilitates bonding with said PDMS material.

15. The device of claim 9, wherein said transparent electrode is a thin film electrode.

16. The device of claim 9, wherein said transparent electrode comprises nanoparticles.

17. The device of claim 16, wherein said nanoparticles comprise nanotubes or nanowires.

18. The device of claim 8, wherein said second wall comprises a photoconductive layer responsive to light passed through said transparent electrode to create virtual electrodes that induce dielectrophoresis (DEP) forces sufficient to move a particle in said liquid.

19. The device of claim 8, wherein said second wall comprises:
a photoconductive layer; and
an optoelectronic wetting surface that is an inner surface of said chamber.

20. The device of claim 19, wherein said photoconductive layer of said second wall is responsive to light passed through said transparent electrode to create virtual electrodes that induce dielectrophoresis (DEP) forces that move a droplet of said liquid in said chamber.

21. The device of claim 8, wherein said second wall comprises an array of fixed electrodes each selectively connectable to said biasing voltage source.

22. The device of claim 21, wherein said second wall further comprises an insulating material covering said fixed electrodes.

23. The device of claim 8, wherein said transparent electrode is a thin film electrode.

24. The device of claim 8, wherein said transparent electrode comprises nanoparticles.

25. The device of claim 24, wherein said nanoparticles comprise nanotubes or nanowires.

26. The device of claim 8, wherein said transparent electrode comprises clusters of nanoparticles.

27. The device of claim 8, wherein said transparent electrode comprises nanoparticles embedded in a flexible material.

28. The device of claim 27, wherein said flexible material is a polymer or a silicone.

29. The device of claim 8, wherein said transparent electrode comprises a combination of nanowires and nanoparticles embedded in a flexible material.

30. The device of claim 8 further comprising a biasing voltage source between said transparent electrode and said second wall.

31. The device of claim 9, wherein said transparent electrode comprises clusters of nanoparticles.

32. The device of claim 9, wherein said transparent electrode comprises nanoparticles embedded in a flexible material.

33. The device of claim 32, wherein said flexible material is a polymer or a silicone.

34. The device of claim 9, wherein said transparent electrode comprises a combination of nanowires and nanoparticles embedded in a flexible material.

* * * * *